United States Patent [19]

Kazmierczak et al.

[11] Patent Number: 4,978,699

[45] Date of Patent: Dec. 18, 1990

[54] LIGHT STABILIZING FLAME RETARDANTS

[75] Inventors: Robert T. Kazmierczak; Ronald E. MacLeay, both of Williamsville, N.Y.

[73] Assignee: Atochem North America, Inc., Philadelphia, Pa.

[21] Appl. No.: 261,442

[22] Filed: Oct. 24, 1988

[51] Int. Cl.$^5$ ............... C08K 5/3417; C08K 5/3435; C07D 401/00

[52] U.S. Cl. .................................. 529/99; 524/103; 546/16; 546/187; 546/200; 546/208; 546/242; 546/244; 546/245; 546/247

[58] Field of Search .............. 524/99, 103; 546/16, 546/187, 200, 208, 242, 244, 245, 247

[56] References Cited

U.S. PATENT DOCUMENTS

| | | | |
|---|---|---|---|
| 3,205,196 | 9/1965 | Creighton | 524/165 |
| 3,240,792 | 3/1966 | Patrick et al. | 549/246 |
| 3,313,763 | 4/1967 | Creighton et al. | 524/94 |
| 3,623,495 | 11/1971 | Erb | 220/89 A |
| 3,639,334 | 2/1972 | Holoch | 524/147 |
| 3,887,518 | 6/1975 | Rosenberger et al. | 524/194 |
| 3,894,988 | 7/1975 | Anderson et al. | 524/208 |
| 3,899,491 | 8/1975 | Ramey et al. | 524/100 |
| 4,003,862 | 1/1977 | Albright | 521/85 |
| 4,147,689 | 4/1979 | Thomspon et al. | 524/193 |
| 4,153,596 | 5/1979 | Oertel et al. | 524/99 |
| 4,210,146 | 5/1985 | Hansen | 524/89 |
| 4,223,147 | 9/1980 | Oertel et al. | 524/102 |
| 4,226,999 | 10/1980 | Malherbe et al. | 524/102 |
| 4,374,220 | 2/1983 | Sonnenberg | 524/94 |
| 4,464,240 | 8/1984 | Hansen | 524/94 |
| 4,465,571 | 8/1984 | Hansen | 524/89 |
| 4,535,170 | 8/1985 | Sonnenberg | 548/462 |
| 4,581,396 | 4/1986 | Sonnenberg | 524/87 |
| 4,644,066 | 2/1987 | Sonnenberg | 548/462 |
| 4,692,486 | 9/1987 | Gugumus | 524/106 |
| 4,730,017 | 3/1988 | Avar | 524/103 |
| 4,822,883 | 4/1989 | Myers | 524/103 |
| 4,824,884 | 4/1989 | MacLeay et al. | 524/103 |

FOREIGN PATENT DOCUMENTS 0188767 7/1988 European Pat. Off. .
2546775 8/1975 Fed. Rep. of Germany .

OTHER PUBLICATIONS

D. S. Pratt et al., "Phthalic Acid Derivatives: Constitution and Color, XIV.: Some Derivatives of Tetra--Bromophthalimide", *Journal of American Chemical Society*, vol. 40, pp. 1415-1425 (1918).

Z. Slama, "Influence of Traces of Copper and Iron on the Photooxidative Aging of Poly(Phenylene Oxide) and Its Mixtures with Impact-Proof Polystyrene", Plaste Kautsch, vol. 26(5), pp. 256-257 (1979), CA 91:92331p Only.

Kirk-Othmer, "Flame Retardants (Halogenated): Additive Flame Retardants", *Encyclopedia of CHemical Technology*, 3rd ed., vol. 14, pp. 384-387.

S. M. Spatz et al., "Some N-Substituted Tetrabromophthalimide Fire-Retardant Additives", *Industrial and Engineering Chemistry, Producer Research Development*, vol. 8, (14), pp. 397-398 (1969).

*Primary Examiner*—Kriellion Morgan
*Attorney, Agent, or Firm*—Panitch, Schwarze, Jacobs & Nadel

[57] ABSTRACT

This invention provides novel hindered amine light stabilizers with flame retardant properties. The compounds of this invention protect polymeric compositions against the degradative effects of heat and light and simultaneously improve the flammability rating of the polymeric composition, while also contributing antioxidant and metal deactivation properties to the polymeric compositions.

The compositions of this invention are prepared by reacting halogenated flame retardant containing a cyclic anhydride group with hindered amine light stabilizers containing primary amino or reactive hydrazido functional groups. The preparation of the novel compositions may be carried out in inert solvents or in inert polymeric compositions in a melt blending step.

18 Claims, No Drawings

LIGHT STABILIZING FLAME RETARDANTS

BACKGROUND OF THE INVENTION

1. Field of the Invention

The present invention relates to novel light stabilizing flame retardants, and more particularly, to hindered amine light stabilizing groups which are bonded to halogenated flame retardants, and methods for preparing the same. Further, the present invention is directed to methods for stabilizing polymers or copolymers against the deleterious effects of heat, light and/or combustion.

2. Description of the Prior art

Flame retardancy using bis-imides has been disclosed by several sources. For example, British Pat. No. 1,287,934 discloses the use of bis-imides as flame retardants for polymers of olefinioally unsaturated aromatic monomers, such as polystyrene and styrene copolymers. Tetrahalophthalimides (halogen-containing bis-imides) have been used as flame retardants in high melting polymers as disclosed in U.S. Pat. No. 4,581,396. D. S. Pratt et al., "Phthalic Acid Derivatives: Constitution and Color, Some Derivatives of Tetrabromophthalimide," Journal of the American Chemical Society, 40:1415 (1918) and S. M. Spatz, et al., "Some N-Substituted Tetrabromophthalimide Fire Retardant Additives", Industrial and Engineering Chemistry; Product Research Development, Vol. 8, No.14, 397–398 (1969), both specifically disclose tetrabromophthalimide. Spatz additionally disclose several specific alkyl tetrabromophthalimides. Other tetrahalophthalimides are disclosed in U.S. Pat. Nos. 3,623,495; 3,313,763; and 3,240,792.

The combination of flame retardant imides with groups bonded thereto have been described. For example, European Patent Application No. 188,767 discloses N-substituted tetrahalophthalimides where the substituent on the nitrogen is an alkyl trialkoxysilane. In addition, a U.S. Pat. No. 4,003,862 discloses N-substituted tetrahalophthalimides where the substituent on the nitrogen is an alkyl haloalkylphosphate. Further, U.S. Pat. No. 4,520,146 and German Offenlegungsschrift No. 2,506,775 disclose N-substituted tetrahalophthalimides where the nitrogen substituent contains a hindered phenol antioxidant group.

European Patent Application No. 101,785 (CA 101 24547p) also discloses N-substituted tetrahalophthalimides where the substituent on the nitrogen is a tetrazole group (a blowing agent).

U.S. Pat. No. 4,465,571 further discloses imides of chlorendic anhydride where the nitrogen substituents are thiodipropionyl amino groups. These compounds are claimed to be useful flame retardants and antioxidants for polymers such as polyolefins as well as synergists for antioxidants used in the polymers.

None of the prior art, however, discloses N-substituted halophthalimides or N-substituted halonorbornene dicarboximides where the nitrogen substituent contains a light stabilizer group, specifically a hindered amine light stabilizer group.

Synthetic polymers, such as polyolefins (e.g.: polyethylene and polypropylene) styrenics (e.g.: polystyrene, rubber modified polystyrene and acrylonitrile-butydiene-styrene (ABS)), polycarbonates, polyesters and polyphenylene ethers, to name a few, are subject to degradation and discoloration upon exposure to heat and/or light with consequent deterioration of mechanical and other properties. These compounds are highly flammable and it is desirable to render them flame retardant.

Hindered amine light stabilizers having the 2,2,6,6-tetraalkylpiperidinyl structure have been found to be very effective in stabilizing polymers, such as the examples listed above, against the deleterious effects of heat and light, while tetrahalophthalimides and halonorbornene dicarboximides are known flame retarding additives for these polymers, among other polymers. In addition, the diacylhydrazide function is known to provide a particularly useful antioxidant function (see U.S. Pat. No. 3,639,334) and also acts as a metal deactivator by chelating metal ions, such as copper ions (see U.S. Pat. Nos. 4,147,689; 4,465,571 and 3,887,518), which metal ions are known to accelerate the photooxidative degradation of many polymers (see, e.g., Z. Slama, Plaste Kantsch., (1979) 25:256 CA 91:92331p).

It would be desirable to have a hindered amine light stabilizing group attached to a flame retardant group by an N-(acylamino)imide linkage or a diacylhydrazide linkage to protect polymer systems from the effects of light, heat and combustion.

SUMMARY OF THE INVENTION

According to the present invention, novel light stabilizing flame retardants comprise a hindered amine light stabilizing group bonded to a halogenated flame retardant group forming an amic acid, an N-(acylamino)amic acid, an imide or an N-(acylamino)imide.

One aspect of the present invention relates to the reaction product of a hindered amine light stabilizer having a primary amino group or a reactive hydrazido group (i.e., unsubstituted terminal nitrogen) and a halogenated flame retardant containing a cyclic anhydride group where the hindered amine light stabilizer is bonded to the halogenated flame retardant to form an amic acid, an N-(acylamino)amic acid, an imide or an N-(acylamino)imide.

Another aspect of the present invention relates to a novel light stabilizing flame retardant comprising a hindered amine light stabilizer of Formula I:

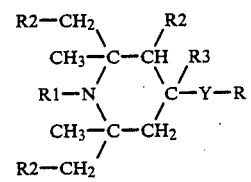

where R, R1, R2, R3, Q, X and Y are herein defined.

Another aspect of the present invention is a process for preparing the novel light stabilizing flame retardants described above comprising reacting a halogen-substituted flame retardant of Formula VII or VIII

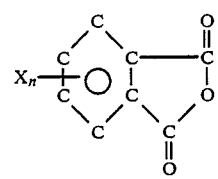

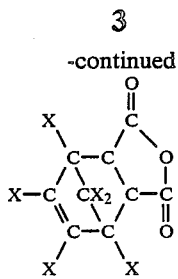

VIII wherein X and n are defined herein with a light stabilizer of Formula IX having a hindered amine light stabilizing group, a primary amino group or a reactive hydrazido group:

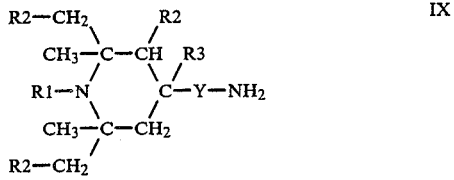

IX wherein R1, R2, R3 and Y are defined herein, under conditions effective to form an (acylamino)amic acid. The (acylamino)amic acid may be heated to form an (acylamino)imide.

Still another aspect of the present invention is a polymer composition comprising a flammable thermoplastic resin which is subject to photooxidative degradation, and a light stabilizing flame retardant as described above, the light stabilizing flame retardant being present in an amount effective to stabilize the polymer composition from the effects of photooxidation and effective to decrease the flammability of the polymer composition.

DEFINITIONS

As used herein, the term "(acylamino)amic acid" refers to the reaction product of a compound having a primary amino group or a reactive hydrazido group and a compound having a cyclic anhydride group.

As used herein, the term "amic acid" refers to the reaction product of a compound having a primary amino group and a compound having a cyclic anhydride group.

As used herein, the term "N-(acylamino)amic acid" refers to the reaction product of a compound having a reactive hydrazido group and a compound having a cyclic anhydride group.

As used herein, the term "(acylamino)imide" refers to a product resulting from the imidization of an (acylamino)amic acid by heating with the resultant loss of a water molecule and ring formation with two carbonyl groups attached to the same nitrogen atom.

As used herein, the term "imide" refers to a product resulting from the imidization of an amic acid by heating with the resultant loss of a water molecule and ring formation with two carbonyl groups attached to the same nitrogen atom.

As used herein, the term "N-(acylamino)imide" refers to a product resulting from the imidization of an N-(acylamino)amic acid by heating with the resultant loss of a water molecule and ring formation with two carbonyl groups attached to the same nitrogen atom.

As used herein, the term "reactive hydrazido group" refers to a hydrazide compound having an unsubstituted terminal nitrogen in the hydrazine portion of the molecule, such as acylhydrazines, semicarbazides and carbazates, for example.

DETAILED DESCRIPTION OF THE PREFERRED EMBODIMENTS

In accordance with the present invention, light stabilizing flame retardants comprise the reaction product of a hindered amine light stabilizer having a primary amine light reactive hydroazido group and a halogenated flame retardant having a cyclic anhydride group. The hindered amine light stabilizers are generally of Formula I:

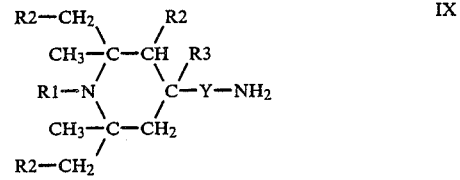

I wherein
R is a halogen-substituted flame retardant radical of Formula II, III, IV or V:

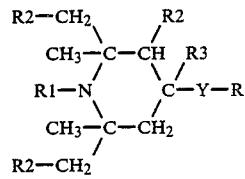

II

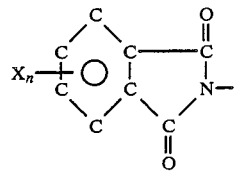

III

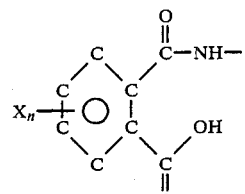

IV

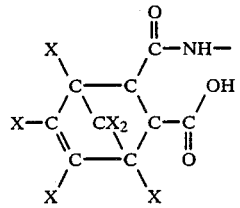

V wherein
X is chlorine or bromine or combinations thereof;
n is an integer from 1 to 4;
R1 is hydrogen, an alkyl radical of 1 to 20 carbons, an alkenyl radical of 3 to 6 carbons, an aralkyl radical of 7 to 12 carbons, an aliphatic acyl radical of 1 to 10 carbons, an aromatic acyl radical of 7 to 13 carbons, an alkoxy carbonyl radical of 2 to 9 carbons, an aryloxy carbonyl radical of 7 to 13 carbons, a hydroxyalkyl radical of 1 to 5 carbons or an epoxyalkyl radical of 3 to 6 carbons;

R2 is hydrogen or an alkyl radical of 1 to 4 carbons;

R3 is hydrogen, hydroxyl or an alkoxy radical of 1 to 4 carbons;

when R3 is hydrogen, Y is a direct bond or a divalent radical —Z—R4—C(=O)—N(R5)—, —Z—C(=O)—N(R5)—, —Z—C(=O)—R6—C(=O)—N(R5)—, —R4—C(=O)—N(R5)— or —C(=O)—N(R5)—, where Z is —O—, —N(R7)—, or —N(R7)—R8—N(R7)—;

when R3 is hydroxyl or alkoxy, Y is a divalent radical —R4—C(=O)—N(R5)— or —C(=O)—N(R5)—; the orientation of Y being such that the left end of the diradical is bonded to the hindered amine group and the right end of the diradical is bonded to the halogen-substituted flame retardant radical;

R4 is an alkylene diradical of 1 to 4 carbons;

R5 is hydrogen, a primary alkyl radical of 1 to 8 carbons, a secondary alkyl radical of 3 to 8 carbons, an aralkyl radical of 7 to 12 carbons, or a cycloalkyl radical of 5 to 12 carbons;

R6 is a direct bond, a substituted or unsubstituted alkylene diradical of 1 to 14 carbons, a substituted or unsubstituted oxydialkylene diradical of 4 to 20 carbons, a substituted or unsubstituted thiodialkylene diradical of 4 to 10 carbons, a substituted or unsubstituted alkenylene diradical of 2 to 10 carbons, or a substituted or unsubstituted o-, m-, or p-phenylene diradical; optional substituents for R6 comprising a lower alkyl radical of 1 to 4 carbons, a lower alkoxy radical of 1 to 4 carbons, hydroxy, bromine, chlorine, a mercapto radical or a lower alkylmercapto radical of 1 to 4 carbons;

R7 is hydrogen, an alkyl radical of 1 to 10 carbons, an aryl radical of 6 to 12 carbons, an aralkyl (arylalkyl) radical of 7 to 12 carbons or a cycloalkyl radical of 5 to 12 carbons; and R8 is an alkylene diradical of 2 to 12 carbons.

Further, the hindered amine light stabilizing flame retardants of the present invention can occur as the acid addition salt of Formula I above and have a Formula VI:

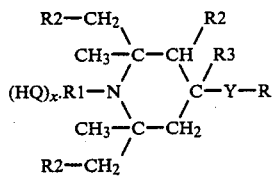

wherein R, R1, R2, R3 and Y are as previously described;

Q is R9—C(=O)—O⁻;

R9 is an alkyl radical of 1 to 4 carbons; and x is 0 or 1 with the proviso that x is 0 when R1 is an acyl radical, an alkoxycarbonyl radical or an aryloxycarbonyl radical.

Preferably, R is 2-carboxy-tetrabromobenzoylamino, 2-carboxytetrachlorobenzoylamino, 1,4,5,6,7,7-hexachloro-5-norbornene-3-carboxy-2-carbonylamino, tetrabromophthalimido, tetrachlorophthalimido or 1,4,5,6,7,7-hexachloro-5-norbornene-2,3-dicarboximido; R1 is hydrogen, methyl, acetyl, benzoyl, 2-hydroxyethyl, phenoxycarbonyl, or benzyl; R2 is hydrogen or methyl; R3 is hydrogen; Y is a direct bond, —Z—R4C—(=O)—N(R5)— or —Z—C(=O)—R6—C(=O)—N(R5)—; Z is —N(R7)—; R4 is —(CH2)$_b$— where b is 1 or 2; R5 and R7 are hydrogen; R6 is a direct bond or —(CH2)$_b$—, where b is as previously defined; HQ is acetic acid; and x is 0 or 1 when R1 is hydrogen or methyl.

More preferably, R is tetrabromophthalimido; R1 is hydrogen or methyl; Y is a direct bond, —Z—R4—C(=O)—N—(R5)— or —Z—C(=O)—R6—C(=O)—N(R5)—; Z is —N(R7)—; R2, R3, R5 and R7 are hydrogen; R4 is —(CH2)$_b$— where b is 1 or 2; R6 is a direct bond; HQ is acetic acid; and x is 0 or 1.

The novel compounds of this invention combine the light stabilizing properties of the 2,2,6,6-tetraalkylpiperidyl structure and the flame retarding properties of the halophthalimides and halonorbornene dicarboximides.

In addition, the novel compounds of this invention where the hindered amine light stabilizing group is attached to the nitrogen of the haloimide by a N-(acylamino) group will provide added stabilization against degradation by heavy metals. N-(acylamino)imides are known stabilizers against degradation by heavy metals. Likewise the novel compounds of this invention where the hindered amine light stabilizing group is attached to the halogenated portion of the molecule by a N,N'-diacylhydrazide functionality (i.e. the amic acid stage where cyclization to the imide has not occurred) will provide additional antioxidant properties and heat stabilization to the polymer composition as well as stabilization against heavy metal degradation.

The novel compounds of this invention are nonvolatile and are not readily lost from polymers while processing at high temperature (typically about 200°–300° C.). The novel compounds are prepared by reacting bromo- or chloro-substituted phthalic or norbornene dicarboxylic anhydrides with hindered amine light stabilizers containing primary amine or reactive hydrazido groups.

Examples of the novel light stabilizing flame retardants of this invention include, without limitation, the following list:

(1) N-(1,2,2,6,6-pentamethyl-4-piperidinyl)-4-bromophthalimide;

(2) N-(1,2,2,6,6-pentamethyl-4-piperidinyl)-4-chlorophthalimide;

(3) N-(1-acetyl-2,2,6,6-tetramethyl-4-piperidinyl)tetrabromophthalimide;

(4) 2-carboxy-N-(1,2,2,6,6-pentamethyl-4-piperidinyl)-tetrachlorophthalamide;

(5) 3-carboxy-N-(2,2,6,6-pentamethyl-4-piperidinyl)-1,4,5,6,7,7-hexachloro-5-norbornene-2-carboxamide;

(6) N-(1,2,2,6,6-pentamethyl-4-piperidinyl)-N'-tetrabromophthalimidooxamide;

(7) N-(1,2,2,6,6-pentamethyl-4-piperidinyl)-N'-tetrabromophthalimidosuccinamide;

(8) N-(1-acetyl-2,2,6,6-tetramethyl-4-piperidinyl)-N'-tetrabromophthalimidoadipamide;

(9) N-(1-benzyl-2,2,6,6-tetramethyl-4-piperidinyl)-N'-tetrachlorophthalimidomalonamide;

(10) N-(1,2,2,6,6-pentamethyl-4-piperidinyl)-N'-1,4,5,6,7,7-hexachloro-5-norbornene-2,3-dicarboximidooxamide;

(11) N-(1-acetyl-2,2,6,6-tetramethyl-4-piperidinyl)-N'-1,4,5,6,7,7-hexachloro-5-norbornene-2,3-dicarboximidosuccinamide;

(12) 3-(1,2,2,6,6-pentamethyl-4-piperidinylamino)-N-tetrabromophthalimidopropionamide;
(13) 2-(1,2,2,6,6-pentamethyl-4-piperidinylamino)-N-tetrachlorophthalimido-acetamide;
(14) 3-(1,2,2,6,6-pentamethyl-4-piperidinylamino)-N-(1,4,5,6,7,7-hexachloro-5-norbornene-2,3-dicarboximido)propionamide;
(15) N-(2,2,6,6-tetramethyl-4-piperidinyl)-N'-tetrabromophthalimido-urea;
(16) N-(1,2,2,6,6-pentamethyl-4-piperidinyl)-N'-tetrachlorophthalimido-urea;
(17) N-(2,2,6,6,-tetramethyl-4-piperidinyl)-N'-4,5,6,7,7-hexachloro-5-norbornene-2,3-dicarboximido-urea;
(18) N-(1,2,2,6,6-pentamethyl-4-piperidinyl)-N'-(2-carboxy-3,4,5,6tetrabromo)benzoylamino]oxamide;
(19) 2,2,6,6-tetramethyl-4-piperidinyl N-tetrabromophthalimidocarbamate;
(20) N-(1-phenoxycarbonyl-2,2,6,6-tetramethyl-4-piperidinyl)-N'-tetrabromophthalimidooxamide;
(21) N-(2,6-diethyl-2,3,6-trimethyl-4-piperidinyl)tetrabromophthalimide;
(22) N-(2,6-diethyl-2,3,6-trimethyl-4-piperidinyl)-1,4,5,6,7,7-hexachloro-5-norbornene-2,3-dicarboximide;
(23) N-[4-(2,2,6,6-tetramethyl-4-piperidinylamino)-butyl]-N'-methyl-N'-(tetrabromophthalimido)oxamide;
(24) N-butyl-N-(2,2,6,6-tetramethyl-4-piperidinyl)-N'-cyclo hexyl-N'-(tetrabromophthalimido)oxamide;
(25) N-(tetrabromophthalimido)-1-allyl-2,2,6,6-tetramethyl-4-hydroxy-4-piperidinylcarboxamide;
(26) N-benzyl-N-(tetrabromophthalimido)-3-[1-(2-hydroxyethyl)-2,2,6,6-tetramethyl-4-methoxy-4piperidinyl]propionamide; and
(27) N-methyl-N-(tetrabromophthalimido)-2-(1-benzoyl-2,2,6,6-tetramethyl-4-piperidinylamino)acetamide.

The light stabilizing flame retardants of this invention are useful additives for the stabilization of polymeric systems or materials which are normally subject to thermal, oxidative or actinic light degradation. They are also useful as flame retarding additives to improve the flammability rating of flammable polymeric compositions. They may be used with synergists for halogenated flame retardants (e.g.: the oxides of Group V elements) to further enhance the flammability ratings of flammable polymeric compositions as well as supplementary flame retardants. They are particularly useful in poly(phenylene oxide) blends.

Non-limiting examples of polymeric materials that may be stabilized by the novel light stabilizing flame retardants include:

(1) polyolefins, such as high, low and linear low density polyethylene, which may be optionally crosslinked, polypropylene, polyisobutylene, poly(methylbutene-1), polyacetylene and in general polyolefins derived from monomers having from two to about ten carbon atoms and mixtures thereof;

(2) polyolefins derived from diolefins, such as polybutadiene and polyisoprene;

(3) copolymers of mono or diolefins, such as ethylene propylene, propylene-butene-1, propyleneisobutylene and ethylene-butene-copolymers;

(4) terpolymers of ethylene and propylene with dienes (EPDM), such as butadiene, hexadiene, dicyclopentadiene and ethylidenenorbornene;

(5) copolymers of alpha-olefins with acrylic or methacrylic acids or their derivatives, such as ethylene-acrylic acid, ethylene-methacrylic acid and ethylene-ethyl acrylate copolymers;

(6) styrenic polymers, such as polystyrene (PS) and poly(p-methylstyrene);

(7) styrenic copolymers and terpolymers, such as styrene-butadiene (SBR), styrene-allyl alcohol and styrene acrylonitrile (SAN), styrene-acrylonitrile-methacrylate terpolymer, styrene-butadiene-styrene block copolymers (SBS);

(8) rubber modified styrenics, such as styrene acrylonitrile copolymers modified with acrylic ester polymers (ASA);

(9) graft copolymers of styrene on rubbers, such as polybutadiene (HIPS), polyisoprene or styrene-butadiene-styrene block copolymers (Stereon ™ products available from Firestone Synthetic Rubber and Latex Co.);

(10) graft copolymers of styrene-acrylonitrile on rubbers, such as butadiene (ABS), polyisoprene or styrene-butadiene-styrene block copolymers;

(11) graft copolymers of styrene-methyl methacrylate on rubbers, such as polybutadiene (MBS), butadiene-styrene radical block copolymers (e.g.: KRO 3 of Phillips Petroleum Co.), selectively hydrogenated butadiene-styrene block copolymers (e.g.: Kraton G from Shell) and mixtures thereof;

(12) polymers and copolymers derived from alpha, beta-unsaturated acids, anhydrides, esters, amides and nitriles or combinations thereof, such as polymers or copolymers of acrylic and methacrylic acids, alkyl and/or glycidyl acrylates and methacrylates, acrylamide and methacrylamide, acrylonitrile, maleic anhydride, maleimide, the various anhydride containing polymers and copolymers described in this disclosure, copolymers of the above polymers and various blends and mixtures thereof as well as rubber modified versions of the above polymers and copolymers;

(13) polymers and copolymers derived from unsaturated alcohols or their acylated derivatives, such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene vinyl alcohol copolymers;

(14) polymers and copolymers derived from unsaturated amines, such as poly(allyl melamine);

(15) polymers and copolymers derived from epoxides, such as polyethylene oxide, polypropylene oxide and copolymers thereof as well as polymers derived from bis glycidyl ethers;

(16) poly(phenylene oxides), poly(phenylene ethers) and modifications thereof containing grafted polystyrene or rubber as well as their various blends with polystyrene, rubber modified polystyrenes or nylon;

(17) polycarbonates and especially the aromatic polycarbonates, such as those derived from phosgene and bisphenols such as bisphenol-A, tetrabromobisphenol-A and tetramethylbisphenol-A;

(18) polyesters derived from dicarboxylic acids and diols and/or hydroxycarboxylic acids or their corresponding lactones, such as polyalkylene phthalates (e.g.: polyethylene terephthalate (PET), polybutylene terephthalate (PBT) and poly(1,4-dimethylcyclohexane terephthalate) or copolymers thereof) and polylactones, such as polycaprolactone;

(19) polyarylates derived from bisphenols (e.g. bisphenol-A) and various aromatic acids, such as isophthalic and terephthalic acids or mixtures thereof;

(20) aromatic copolyester carbonates having carbonate as well as ester linkages present in the backbone of the polymer, such as those derived from bisphenols, iso and terephthaloyl chlorides and phosgene;

(21) polyurethanes and polyureas;

(22) polyacetals, such as polyoxymethylenes and polyoxymethylenes which contain ethylene oxide as a comonomer;

(23) polysulfones, polyethersulfones and polyimidesulfones;

(24) polyamides and copolyamides which are derived from diamines and dicarboxylic acids and/or from aminocarboxylic acids or the corresponding lactones, such as nylons 6, 6/6, 6/10,11 and 12;

(25) polyimides, polyetherimides, polyamideimides and copolyetheresters;

(26) crosslinked polymers which are derived from aldehydes on the one hand and from phenols, ureas and melamine on the other hand, such as phenolformaldehyde, urea-formaldehyde and melamineformaldehyde resins;

(27) alkyl resins, such as glycerol-phthalic acid resins and mixtures thereof with melamineformaldehyde resins;

(28) unsaturated polyester resins which are derived from copolyesters of saturated and unsaturated dicarboxylic acids with polyhydric alcohols as well as from vinyl compounds as crosslinking agents and also the halogen-containing, flame resistant modifications thereof; and

(29) natural polymers, such as natural rubber, cellulose as well as the chemically modified homologous derivatives thereof, such as cellulose acetates, cellulose propionates, cellulose butyrates and the cellulose ethers, such as methyl and ethyl cellulose.

Preferably the compounds of this invention are used to stabilize polymeric materials against the deleterious effects of heat and light and simultaneously improve the flammability rating of the polymeric material.

The light stabilizers and flame retardants of this invention may be incorporated into or applied onto the above polymeric materials by techniques which are standard or known to those skilled in the art. See, for example, J. M. Lyons, "The Chemistry and Uses of Fire Retardants" (Wiley-Interscience, New York, 1970) and Z. E. Jalles, "Bromine and Its Compounds" (Academic Press, New York, 1966). In addition, the light stabilizers and flame retardants can be generated in inert polymeric substances by reacting the halogenated anhydride with the functionalized hindered amine light stabilizer in the molten inert polymeric substance.

When used to stabilize the polymeric composition against heat and light it is advisable to have about 0.01 to about 5% by weight of the 2,2,6,6-tetraalkylpiperidine moiety present in the polymeric composition. An advantageous range is from about 0.05 to about 2% by weight of the 2,2,6,6-tetraalkylpiperidine portion of the molecule in the final composition. In most cases from about 0.1 to about 1% by weight is sufficient.

The flammability rating of the stabilized compositions can be further enhanced by the addition of other halogenated flame retardants (see Kirk-Othmer, Encyclopedia of Chemical Technology, Third Edition, Vol. 10, pp 384–387), small amounts of alkali metal sulfonic acid salts or alkali metal carboxylic acid salts (European Patent Application No. 0,188,767) or preferably by the addition of synergists for halogenated flame retardants, such as the oxides or halides of the metals of Groups IVA and VA of the Periodic Table, (i.e., oxides and halides of antimony, tin, bismuth, arsenic, lead, germanium, such as antimony trioxide, antimonyoxychloride and those disclosed in U.S. Pat. Nos. 3,205,196 and 3,894,988).

It is presently preferred that the compounds of this invention will be used in amounts about 0.5% to about 5% by weight to stabilize the polymeric compositions against the deleterious effects of heat and light and simultaneously improve the flammability rating of the polymeric composition. If the flame resistance has to be further enhanced auxiliary flame retardants and synergists for halogenated flame retardants should be employed.

At times it may be beneficial to add extraneous additives which will act as synergists with the hindered amine light stabilizing groups. The light stabilizing flame retardants of this invention can be used together with other additives to further enhance the properties of the finished polymer. Examples of other additives that can be used in conjunction with the stabilizers of this invention include, for example: (a) antioxidants, such as alkylated monophenols, alkylated hydroquinones, hydroxylated thiodiphenyl ethers, alkylidene-bis-phenols, hindered phenolic benzyl compounds, acylaminophenols, esters of 3-(3,5-di-t-butyl-4-hydroxyphenyl)-propionic acid, esters of 3-(5-t-butyl-4-hydroxy-3-methylphenyl)propionic acid, 3-(3,5-di-t-butyl-4-hydroxyphenyl)propionic acid amides; (b) UV absorbers and light stabilizers, such as 2-(2,-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, auxiliary hindered amine light stabilizers; and (c) other additives, such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, other organic and inorganic flame retardants and non-dripping agents, melt flow improvers and antistatic agents and other polymer additives known in the art. Numerous examples of suitable additives of the above type are given in Canadian Pat. No. 1,190,038.

GENERAL PREPARATIVE METHODS

The light stabilizing flame retardants of the present invention are generally prepared by reacting a halogen-substituted (preferably bromine or chlorine) phthalic or 5-norbornene dicarboxylic anhydride of Formula VII or VIII:

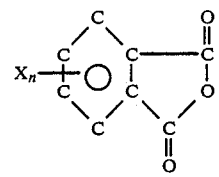

VII

-continued

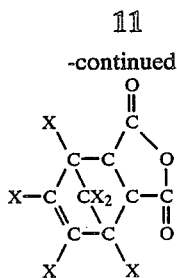

VIII wherein X and n are as previously defined, with a hindered amine light stabilizer of Formula IX having a primary amino group or a reactive hydrazido group:

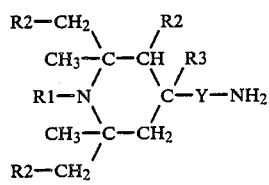

IX where R1, R2, R3 and Y are as previously defined, under conditions effective to form an (acylamino)amic acid or an (acylamino)imide.

Examples of suitable bromo- or chloro-substituted anhydrides include the following non-limiting examples:
tetrabromophthalic anhydride,
tetrachlorophthalic anhydride,
dibromophthalic anhydride,
dichlorophthalic anhydride,
4-bromophthalic anhydride,
4-chlorophthalic anhydride,
dibromo-dichlorophthalic anhydride,
bromo-trichlorophthalic anhydride,
chloro-tribromophthalic anhydride, and
1,4,5,6,7,7-hexachloro-5-norbornene-2,3-dicarboxylic anhydride.

Examples of suitable hindered amine light stabilizers containing a reactive amino group (i.e., where Y is a direct bond) include the following non-limiting examples:
4-amino-2,2,6,6-tetramethylpiperidine,
4-amino-1,2,2,6,6-pentamethylpiperidine,
4-amino-1-benzyl-2,2,6,6-tetramethylpiperidine,
4-amino-2,6-diethyl-2,3,6-trimethylpiperidine,
1-acetyl-4-amino-2,2,6,6-tetramethylpiperidine, and
4-amino-1-butyl-2,2,6,6-tetramethylpiperidine.

Examples of suitable hindered amine light stabilizers containing a reactive hydrazido group include the following non-limiting examples:
3-(2,2,6,6-tetramethyl-4-piperidinylamino)-propionhydrazide,
3-(1,2,2,6,6-pentamethyl-4-piperidinylamino)-propionhydrazide,
(2,2,6,6-tetramethyl-4-piperidinylamino)acetyl-hydrazide,
(1,2,2,6,6-pentamethyl-4-piperidinylamino)-acetylhydrazide,
N-(2,2,6,6-tetramethyl-4-piperidinyl)hydrazinecarboxamide,
N-(1,2,2,6,6-pentamethyl-4-piperidinyl)hydrazinecarboxamide,
N-(2,2,6,6-tetramethyl-4-piperidinyl)-N'-aminooxamide,
N-(1,2,2,6,6-pentamethyl-4-piperidinyl)-N'-aminooxamide,
N-(2,2,6,6-tetramethyl-4-piperidinyl)-N'-aminosuccinamide,
N-(1,2,2,6,6-pentamethyl-4-piperidinyl)-N'-aminosuccinamide,
N-(2,2,6,6-tetramethyl-4-piperidinyl)-N'-aminomalonamide,
N-(1-benzyl-2,2,6,6-tetramethyl-4-piperidinyl)-N'-aminomalonamide,
N-(1-benzyl-2,2,6,6-tetramethyl-4-piperidinyl)-N'-aminooxamide,
N-(1-betahydroxyethyl-2,2,6,6-tetramethyl-4-piperidinyl)-N'-aminooxamide,
N-(2,6-diethyl-2,3,6-trimethyl-4-piperidinyl)-N'-aminoadipamide,
N-(1-acetyl-2,2,6,6-tetramethyl-4-piperidinyl)-N'-aminooxamide,
3-(1-acetyl-2,2,6,6-tetramethyl-4-piperidinylamino)propionhydrazide,
(2,2,6,6-tetramethyl-4-piperidinyloxy)acetylhydrazide,
(1,2,2,6,6-pentamethyl-4-piperidinyloxy)acetylhydrazide,
3-(2,2,6,6-tetramethyl-4-piperidinyloxy)propionhydrazide,
3-(1,2,2,6,6-pentamethyl-4-piperidinyloxy)propionhyrdazide,
N-(1-acetyl-2,2,6,6-tetramethyl-4-piperidinyl)hydrazinecarboxamide,
N-(1-benzoyl-2,2,6,6-tetramethyl-4-piperidinyl)-N'-aminooxamide,
3-(2-benzoyl-2,2,6,6-tetramethyl-4-piperidinylamino)-propionhydrazide, and
1,2,2,6,6-pentamethyl-4-piperidinyl carbazate.

In view of the disclosure herein, other examples of hindered amine light stabilizers having a primary amino or a reactive hydrazido group may be readily determined by one skilled in the art without undue experimentation.

Preferably, tetrabromophthalic anhydride is reacted with a 2,2,6,6-tetraalkylpiperidine containing a reactive hydrazide functionality at a high enough temperature to form a tetrabromophthalimide with a 2,2,6,6-tetraalkylpiperidine group connected to the imide nitrogen by an acylamino linkage.

General methods for the synthesis of these hydrazido functionalized hindered amine light stabilizers can be found in co-pending patent application Ser. No. 84,602, filed Aug. 12, 1987 now abandoned, assigned to the assignee of the present application, and in U.S. Pat. Nos. 4,223,147; 4,153,596; and 3,899,491.

The halo-substituted anhydrides react with primary amino-functionalized hindered amine light stabilizers to form an amic acid. In similar fashion, the anhydrides react with hydrazido functionalized hindered amine light stabilizers to form an N-(acylamino)amic acid. These reactions generally occur readily and at relatively low temperatures. This may be illustrated by the following equations:

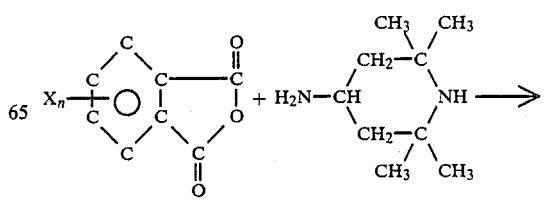

-continued

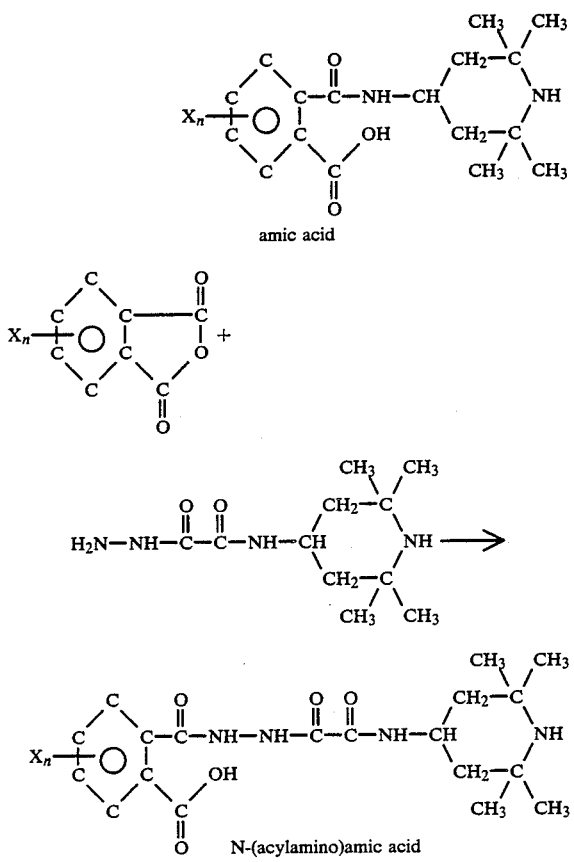
amic acid

When the (acylamino)amic acid (whether from a primary amino or a relative hydrazido light stabilizer) is heated, further reaction occurs in which a molecule of water is lost and a ring is formed with two carbonyl groups attached to the amide nitrogen. The cyclized product from the amic acid is referred to as an imide and the one from the hydrazide is referred to as an N-(acylamino)imide. This may be illustrated by the following equations:

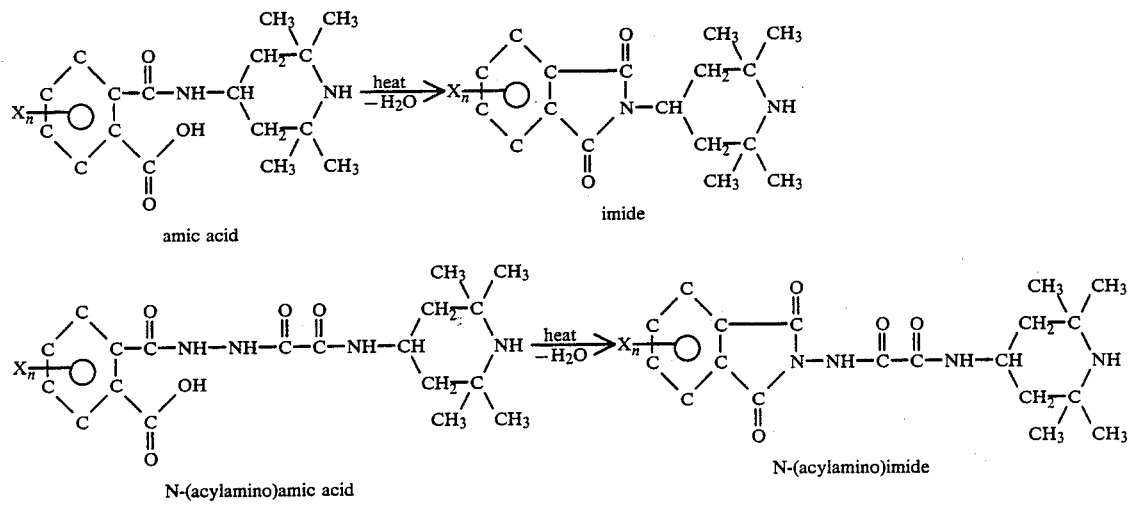

Depending on the substitution of the anhydride and amine (or hydrazide), the cyclization of the (acylamino)amic acid to the (acylamino)imide occurs under a wide range of reaction conditions, particularly reaction temperature and duration. Temperature is usually the dominant factor. Below about 100° C., the (acylamino)amic acid will not convert to the (acylamino)imide without the aid of a co-reactant(s), such as acetic anhydride and sodium acetate. Above about 175° C., an (acylamino)amic acid, once formed, will begin conversion to the (acylamino)imide immediately.

Very short reaction times, like those obtainable in a melt blender or extruder can yield mixtures of both (acylamino)amic acid and (acylamino)imide, depending upon the temperature. At intermediate reaction temperatures of about 100° C. to about 175° C., the reaction duration becomes very important and mixtures of (acylamino)amic acid and (acylamino)imide may result, the amount of each formed depending on reaction duration and temperature. The N-(acylamino)amic acids cyclize to the N-(acylamino)imides more readily and at lower temperatures than the cyclization of the amic acids to the imides.

The reaction of the hindered amine light stabilizers containing primary amino or reactive hydrazido groups with the halo-substituted anhydrides may be carried out in inert solvents such as toluene, xylene, chlorobenzene, mesitylene, dimethylformamide, tetrahydrofuran, N-methyl-2-pyrrolidone, dimethylacetamide and acetic acid. In some cases the reaction may be run in hot water.

If the reaction temperature is not hot enough, the reaction may stop at the intermediate (acylamino)amic acid or only partial conversion of the (acylamino)amic acid to the (acylamino)imide may occur. The (acylamino)amic acids cyclize to the (acylamino)imides if heated to higher temperatures. If the reaction is run in refluxing acetic acid, the acetic acid salts of the (acylamino)imide are generally obtained if the hindered nitrogen is not acylated.

The reaction may also be carried out in a melt blending step in an inert polymeric composition. This is generally accomplished at a temperature above the softening point of the polymeric composition using any conventional melt mixing apparatus such as a plastograph, Banbury mixer, two roll mill, single or twin screw extruder or any other method which applies sufficient heat (e.g.: about 175° to about 300° C.) and shear to the ingredients to obtain a satisfactory blend. Preferably, the reaction is carried out in an inert atmosphere, such as nitrogen.

The polymeric compositions should be void of anhydride, epoxy, hydroxyl, thiol or amino groups to prevent the reactants from reacting with the polymeric composition. Examples of suitable inert polymeric compositions in which the reaction may be run include polystyrene, rubber-modified polystyrene, halogenated polystyrenes, polyolefins such as polyethylene, polypropylene, copolymer thereof, ABS, SAN, MBS, ASA, poly(phenylene oxide), poly(phenylene ethers) and various combinations thereof. When carrying out the reaction in a polymeric composition, it is preferable to use a molar ratio of about 0.9:1 to about 1:0.9 of the halogenated flame retardant containing an anhydride group to the hindered amine light stabilizer. To stabilize the polymer against photooxidation, about 0.5% to about 5% by weight of the light stabilizing flame retardant should be formed relative to the polymer composition. To stabilize the polymer against combustion, the halogen should be present in an amount of about 5% to about 10% halogen by weight relative to the polymer composition.

The reaction may be carried out for times varying from 30 seconds to 48 hours, depending upon the degree of conversion of the (acylamino)amic acid to the (acylamino)imide desired, the reactivity of the functionalized hindered amine light stabilizers, the reaction temperature employed, the presence or absence of a solvent and the use or non-use of a catalyst. Higher reaction temperatures naturally reduce the required reaction time for any particular system of reactants. Preferably the reactions are carried out at temperatures of about 125° to about 225° C.

When the reactions are run in solution, the products are normally isolated by removal of solvent. In the case of insoluble products or slightly soluble products, the solvent is removed by filtration, preferably warm. In the case of soluble products the solvent is removed from the product by evaporation such as on a rotating evaporator under reduced pressure.

The present invention will now be illustrated by reference to the following specific, non-limiting examples.

The following reactants were used in the preparation of the novel compounds for the Examples below:

N-(2,2,6,6-tetramethyl-4-piperidinyl)-N'-aminooxamide was prepared by reacting 4-amino-2,2,6,6-tetramethylpiperidine with an excess of diethyl oxalate, stripping off the unreacted diethyl oxalate and reacting the residue with 80% hydrazine hydrate in methanol. The procedure is described in the above-referenced copending U.S. patent application Ser. No. 84,602.

3-(2,2,6,6-tetramethyl-4-piperidinylamino)propionhydrazide was prepared by the addition of 4-amino-2,2,6,6-tetramethylpiperidine to methyl acrylate followed by hydrazinolysis of the resultant ester. A detailed description can be found in U.S. Pat. No. 4,223,147.

4-Amino-2,2,6,6-tetramethylpiperidine, chlorendic anhydride, tetrachlorophthalic and tetrabromophthalic anhydrides were purchased from Aldrich Chemical Company.

EXAMPLE I

Reaction of Tetrabromophthalic Anhydride with N-(2,2,6,6-tetramethyl-4-piperidinyl)-N'-aminooxamide (A) In Tetrahydrofuran at 35° C.

Into a 250 ml 3-neck round bottom flask, 14.0 grams (0.03 mole) of tetrabromophthalic anhydride and 100 ml of tetrahydrofuran (THF) were added. The flask was equipped with a magnetic stirrer, thermometer and reflux condenser. The mixture was warmed to 35° C. with stirring in a water bath. 7.3 grams (0.03 mole) of N-(2,2,6,6-tetramethyl-4-piperidinyl)-N'-aminooxamide were added over a 5 minute interval. The reaction mixture took on a light yellow color and then turned white again after stirring about 15 minutes. The reaction was stirred 1.5 hours while allowing the temperature to drop back to room temperature. The white milky slurry was filtered and the filter cake, which was still wet with THF, was dried under vacuum. The product was a white powder. The infrared scan of the product had a very weak band at 1710 cm$^{-1}$, a very strong broad band at 1680–1630 cm$^{-1}$, and a relatively weak band at 1520 cm$^{-1}$. The infrared spectrum was consistent with the amic acid structure indicating the product was predominantly N-(2,2,6,6-tetramethyl-4-piperidinyl)-N'-[(2-carboxy-3,4,5,6-tetrabromo)benzoylamino]oxamide. The dry product weighed 22.6 grams, turned yellow upon heating above 170° C. and melted at 199°–208° C. with gas evolution. It appeared that the compound was cyclizing to the imide while evaluating the melting point.

(B) In Refluxing Xylene:

Into a 500 ml 3-neck round bottom flask equipped with a magnetic stirrer, thermometer and Dean Stark trap containing a reflux condenser, 6.96 grams (0.015 mole) tetrabromophthalic anhydride, 3.63 grams (0.015 mole) N-(2,2,6,6-tetramethyl-4-piperidinyl)-N'-aminooxamide and 100 ml xylene were added. The reaction mixture was heated in an oil bath to reflux and azeotroped for 4 hours at 139°–141° C. The reaction mixture was cooled to room temperature and the insoluble was filtered off. The filter cake was slurried in hexane, refiltered and the filter cake was air dried. The product was a yellow powder weighing 10.7 grams. It melted at 221°–227° C. and then resolidified. The infrared scan of the product had strong carbonyl bands at 1750 cm$^{-1}$, 1710 cm$^{-1}$, 1660 cm$^{-1}$ and 1600 cm$^{-1}$. The infrared spectrum was consistent with the imide structure, indicating that ring closure had occurred and the product was predominantly N-(2,2,6,6-tetramethyl-4-piperidinyl)-N'-(3,4,5,6-tetrabromophthalimido)oxamide.

(C) In Refluxing Acetic Acid:

Into a 250 ml 3-neck round bottom flask 14.0 g (0.03 mole) of tetrabromophthalic anhydride and 75 ml of acetic acid were added. The flask was equipped as in part A and warmed to 40° C. The N'-(2,2,6,6-tetramethyl-4-piperidinyl)-N'-aminooxamide was added over about 5 minutes. The reaction was heated in an oil bath and upon reaching 70° C., complete solution was obtained. Shortly thereafter, the reaction mixture solidified into a lard-like material. Upon heating to reflux, the solid mass broke up and stirring resumed. The reaction mixture was refluxed for 2 hours at approximately 120° C. and then cooled to room temperature. The solids were filtered off and washed twice with 200 ml portions of hexane. The filter cake was air dried overnight on a watch glass. The product was a white powder weighing 20.9 g. The infrared scan (nujol mull) of the product contained strong carbonyl bands at 1670, 1710, and 1740 cm$^{-1}$ and a moderate band at 1610 cm$^{-1}$. The infrared spectrum was consistent with the acetic acid salt of N-(2,2,6,6-tetramethyl-4-piperidinyl)-N'-(3,4,5,6tetrabromophthalimido)oxamide.

(D) Conversion of Amic Acid of Example IA to Imide of IB:

A sample of the amic acid prepared in Example IA was heated in a Perkin-Elmer Differential Scanning Calorimeter (DSC) at 20° C./minute under a nitrogen purge. The DSC scan indicated that a reaction began occurring around 150° C. and the reaction peaked at 177° C. A comparison of Fourier Transform Infrared (FTIR) scans of the material before heating and after heating to 208° C. showed that most of the strong broad carbonyl band at 1680–1630 cm$^{-1}$ had converted into two strong sharp bands at 1750 and 1710 cm$^{-1}$ indicating that most of the amic acid had cyclized to the imide, the predominant product produced in Example IB.

EXAMPLE II

Reaction of Tetrachlorophthalic Anhydride with N-(2,2,6,6-tetramethyl-4-piperidinyl)-N'-aminooxamide (A) In Tetrahydrofuran at 35° C.:

The reaction was carried out in the same manner as Example IA except tetrachlorophthalic anhydride (8.6 grams, 0.03 mole) was used instead of tetrabromophthalic anhydride. After drying under vacuum, the filter cake was a white powder and weighed 15.9 grams. The infrared spectrum (nujol mull) of the product had a very weak band at 1715 cm$^{-1}$, very strong bands at 1675 and 1620 cm$^{-1}$ and weaker bands at 1480 cm$^{-1}$ and 1520 cm$^{-1}$. The infrared spectrum was consistent with the amic acid structure, indicating the product was predominantly N-(2,2,6,6-tetramethyl-4-piperidinyl)-N'-[(2-carboxy-3,4,5,6-tetrachloro)benzoylamino]oxamide. The product turned yellow upon heating above 170° C. and melted at 195°–200° C. and then resolidified. It appeared that cyclization was occurring while evaluating the melting point.

(B) In Refluxing Xylene:

8.58 grams (0.03 mole) of tetrachlorophthalic anhydride and 8.5 grams (0.035 mole) of N-(2,2,6,6-tetramethyl-4-piperidinyl)-N'-aminooxamide were refluxed in 130 ml of xylene for 2.5 hours using the procedure of Example I. The product was isolated by cooling the reaction and filtering off the insoluble components as in Example IB. The product was a light yellow powder weighing 16.9 grams and had a melting point of 205°–208° C. The infrared scan of the product had a very strong carbonyl bands at 1750 and 1710 cm$^{-1}$ and weaker bands at 1605 cm$^{-1}$ and 1675 cm$^{-1}$. The infrared spectrum was consistent with the imide structure indicating that ring closure to the imide had occurred and the product was predominantly N-(2,2,6,6-tetramethyl-4-piperidinyl)-N'-(3,4,5,6-tetrachlorophthalimido)oxamide.

(C) In Refluxing Acetic Acid:

The reaction was carried out in the same manner as Example IC except 14.3 g (0.05 mole) tetrachlorophthalic anhydride, 12.75 g (0.05 mole) N-(2,2,6,6-tetramethyl-4-piperidinyl)N'-aminooxamide and 100 ml acetic acid were used. The product was a white powder weighing 31.7 g. The infrared spectrum had strong carbonyl bands at 1620, 1670, and 1740 cm$^{-1}$ and was consistent with the acetic acid salt of N-(2,2,6,6-tetramethyl-4-piperidinyl)-N'-(3,4,5,6-tetrachlorophthalimido)oxamide.

(D) Conversion of Amic Acid of Example IIA to Imide of Example IIB:

A sample of the amic acid prepared in Example IIA was heated in the DSC as in Example ID. The DSC scan indicated a reaction began occurring at around 170° C. and the reaction peaked at 205° C. A comparison of FTIR scans of the material before heating and after heating to 225° C. showed that most of the strong broad carbonyl bands at 1675 and 1620 cm$^{-1}$ had converted into strong, sharp bands at 1745 and 1705 cm$^{-1}$, indicating that most of the amic acid had cyclized to the imide, the predominant product produced in Example IIB.

EXAMPLE II

Reaction of Ohlorendic Anhydride with N-(2,2,6,6-tetramethyl-4-piperidinyl)-N'-aminooxamide (A) In Tetrahydrofuran at 35° C.:

The reaction was carried out in the same manner as Example IA except 11.1 grams (0.03 mole) chlorendic anhydride were used instead of tetrabromophthalic anhydride. After stirring for 3 hours, the reaction was filtered and the filter cake air dried overnight. The product was a white solid weighing 3.9 grams. It turned brown upon heating above 145° C. and melted at 263°–265° C. The infrared spectrum (nujol mull) of the filter cake had a very strong broad carbonyl band at 1670 cm$^{-1}$ and a weaker carbonyl band at 1595 cm$^{-1}$. The infrared spectrum was consistent with the amic acid structure, indicating the filter cake was predominantly N-(2,2,6,6-tetramethyl-4-piperidinyl)-N'-[(3-carboxy-1,4,5,6,7,7-hexachloro-5-norbornene)-2-carbonylamino]oxamide.

11.6 additional grams of the same product were obtained by stripping the tetrahydrofuran filtrate to dryness on a rotating evaporator under reduced pressure. The infrared spectrum of the residue was the same as the infrared spectrum of the filter cake.

(B) In Refluxing Xylene:

18.54 grams (0.05 mole) chlorendic anhydride and 12.2 grams (0.05 mole) of N-(2,2,6,6-tetramethyl-4-piperidinyl)-N'-aminooxamide were refluxed in 150 ml of xylene for 2.5 hours using the procedure of Example IB. The product was isolated by cooling the reaction and filtering off the insoluble components as in Example IB. The product weighed 28.0 grams and had a melting point of 212°–215° C. The infrared spectrum had strong carbonyl bands at 1680 cm$^{-1}$, 1740 cm$^{-1}$ and 1600 cm$^{-1}$ and a sharp weak NH band at 3300 cm$^{-1}$. The anhydride peak of chlorendic anhydride at 1800 cm$^{-1}$ had completely disappeared after 0.5 hour of refluxing the reaction mixture. The infrared spectrum of the product was consistent with the imide structure (strong carbonyl at 1740 cm$^{-1}$), indicating that ring closure of the amic acid had occurred and the product was predominantly N-(2,2,6,6-tetramethyl-4-piperidinyl)-N'-(1,4,5,6,7,7-hexa-chloro-5-norbornene-2,3-dicarboximido)oxamide.

(C) In Refluxing Acetic Acid:

The reaction was carried out in the same manner as in Example IC except 18.9 grams (0.05 mole) chlorendic anhydride, 12.75 grams (0.05 mole) N-(2,2,6,6-tetramethyl-4-piperidinyl)-N'-aminooxamide and 100 ml acetic acid were used. The reaction was refluxed for 2 hours but no solids formed. The acetic acid was stripped off on a rotary evaporator under reduced pressure. The residue was scraped out of the flask, pulverized by mortar and pestle and slurried in 300 ml hexane for 0.5 hour. The slurry was filtered and the filter cake air dried overnight. The product was a tan solid weighing 35.8 grams. The infrared spectrum (nujol mull) of the product had a strong carbonyl band at 1740 cm$^{-1}$ and moderate carbonyl bands at 1675 and 1600 cm$^{-1}$ and was consistent with the acetic acid salt of N-(2,2,6,6-tetramethyl-4-piperidinyl)-N'-(1,4,5,6,7,7-hexachloro-5-norbornene-2,3-dicarboximido)oxamide. The compound slowly evolved acetic acid upon heating above 170° C.

(D) Conversion of Amic Acid of Example IIIA to Imide of Example IIIB:

A sample of the amic acid prepared in Example IIIA was heated in the DSC as in Example ID. The DSC scan indicated a reaction began occurring around 146° C. and the reaction peaked at 62° C. A comparison of FTIR scans of the material before heating and after heating to 171° C. showed that most of the strong carbonyl band at 1670 cm$^{-1}$ had converted into a strong sharp band at 1740 cm$^{-1}$ and a broad weaker band at 1680 cm$^{-1}$, indicating most of the amic acid had cyclized to the imide, the predominant product produced in Example IIIB.

EXAMPLE IV

Reaction of Tetrabromophthalic Anhydride with 4-Amino-2,2,6,6-tetramethylpiperidine (A) In Refluxing Xylene:

Into a 250 ml 3-neck round bottom flask 13.8 grams (0.03 mole) tetrabromophthalic anhydride and 130 ml of xylene were added. The flask was equipped with a magnetic stirrer, thermometer, Dean Stark trap containing a reflux condenser and a dropping funnel containing 5.5 grams (0.035 mole) 4-amino-2,2,6,6-tetramethylpiperidine. The xylene slurry was heated to 110° C. and the tetrabromophthalic anhydride went into solution. The amine was added dropwise from the dropping funnel over an approximately 5 minute interval. A yellow precipitate formed immediately. The reaction mixture was heated to reflux and azeotroped for 2.5 hours. The reaction mixture was cooled to 100° C. and filtered hot. The filter cake was semi-dried and then slurried in 100 ml of hexane and refiltered. The yellow filter cake was air dried overnight. The dry product weighed 19.1 grams and had a melting point of 227°-230° C. The infrared spectrum of the product had strong carbonyl bands at 1655 cm$^{-1}$, and 1605 cm$^{-1}$ indicating the product was primarily the amic acid and ring closure to the imide had not occurred.

The xylene filtrate was stripped to dryness on a rotating evaporator under reduced pressure. The residue weighed 1.9 grams and had a melting point of 203°-205° C. The infrared spectrum of the material had one strong carbonyl at 1715 cm$^{-1}$ and a weak carbonyl band at 1770 cm$^{-1}$. These bands are consistent with the tetrabromophthalimide structure and indicate some of the phthalamic acid cyclized to N-(2,2,6,6-tetramethyl-4-piperidinyl)tetrabromophthalimide during the reflux period.

A sample of the xylene insoluble product was heated in a Perkin Elmer 7 Series Thermal Analysis System DSC under nitrogen to 250° C. The DSC scan indicated an endothermic reaction occurred between 225° C. and 250° C. with a peak at 240° C. A comparison of FTIR scans of the material before and after heating to 250° C. indicated the carbonyl peaks at 1655 cm$^{-1}$ and 1605 cm$^{-1}$ had been converted to a very strong carbonyl peak at 1715 cm$^{-1}$, indicating that the amic acid had been converted to the N-(2,2,6,6-tetramethyl-4-piperidinyl)tetrabromophthalimide.

(B) In Refluxing Acetic Acid:

The reaction was carried out in the same manner as Example IC except 14.0 g (0.03 mole) tetrabromophthalic anhydride, 50 g (0.03 mole) 4-amino-2,2,6,6-tetramethylpiperidine and 75 ml of acetic acid were used. The reaction was refluxed 2 hours, cooled to room temperature and filtered. The filter cake was slurried in 250 ml hexane, filtered and air dried overnight. The product was a white powder and weighed 17.8 g. The infrared spectrum (nujol mull) of the product had a strong carbonyl doublet at 1675-1690 cm$^{-1}$, a moderately strong band at 1610 cm$^{-1}$ and a weak band at 1720 cm$^{-1}$, indicating the product was predominantly the acetic acid salt of the amic acid.

EXAMPLE V

Reaction of Tetrachlorophthalic Anhydride with 4-Amino-2,2,6,6-tetramethylpiperidine (A) In Refluxing Xylene:

Tetrachlorophthalic anhydride (8.57 grams; 0.03 mole) and 4-amino-2,2,6,6-tetramethylpiperidine (5.5 grams; 0.035 mole) were refluxed in 130 ml of xylene using the procedure of Example IV. The insoluble product was isolated by cooling the reaction mixture to 100° C. and filtering the hot solution. The filter cake was slurried in hexane and refiltered as in Example IV. The dry yellow product weighed 11.5 grams and had a melting point of 247°-250° C. The infrared spectrum of the product had strong carbonyl bands at 1665 cm$^{-1}$ and 1640 cm$^{-1}$ and a weak band at 1560 cm$^{-1}$. The infrared spectrum was consistent with the amic acid structure.

The xylene filtrate was stripped to dryness on a rotating evaporator under reduced pressure. The residue weighed 3.2 grams and had a melting point of 155°-158° C. The infrared spectrum of this material had one strong carbonyl band at 1720 cm$^{-1}$ and a weak band at 1770 cm$^{-1}$. These bands are consistent with the tetrachlorophthalimide structure and indicate some of the N-(2,2,6,6-tetramethyl-4-piperidinyl)tetrachlorophthalamic acid had cyclized to the N-(2,2,6,6-tetramethyl-4-piperidinyl)tetrachlorophthalimide during the reflux period.

A sample of the xylene insoluble product was heated in a Perkin-Elmer DSC under nitrogen to 270° C. The DSC scan indicated an endothermic reaction occurred between 225° C. and 265° C. with a peak at 257° C. A comparison of FTIR scans of the material before and after heating to 270° C. indicated the carbonyl peaks at 1665 and 1640 cm$^{-1}$ had been converted to a very strong carbonyl peak at 1720 cm$^{-1}$, indicating that the amic acid had been converted to the imide.

(B) In Refluxing Acetic Acid:

The reaction was carried out in the same manner as Example IVB except 14.3 g (0.05 mole) tetrachlorophthalic anhydride, 8.2 g (0.05 mole) 4-amino-2,2,6,6-tetramethylpiperidine and 100 ml acetic acid were used. The reaction was refluxed for 4 hours but no solids formed. The acetic acid was stripped off on a rotary evaporator under reduced pressure. The residue was scraped out of the flask, pulverized by mortar and pestle, slurried in 300 ml hexane and filtered. After drying overnight, the light yellow product weighed 26.5 g.

The infrared spectrum (nujol mull) of the product had a strong carbonyl band at 1720 cm$^{-1}$ with a weaker shoulder at 1700 cm$^{-1}$. There was also a strong band at 1605 cm$^{-1}$. The infrared scan was consistent with the acetic acid salt of N-(2,2,6,6-tetramethyl-4-piperidinyl)-tetrachlorophthalimide.

EXAMPLE VI

Reaction of Chlorendic Anhydride with 4-Amino-2,2,6,6-tetramethylpiperidine

Chlorendic anhydride (11.1 grams; 0.03 mole) and 4-amino-2,2,6,6-tetramethylpiperidine (5.5 grams; 0.035 mole) were refluxed in 130 ml xylene using the procedure of Example IV. The insoluble product was isolated by cooling the reaction mixture to 100° C. and filtering the hot solution. The filter cake was slurried in hexane and refiltered as in Example IV. The dry product weighed 12.7 grams and melted with charring at 257°-260° C. The infrared spectrum of the product had strong carbonyl bands at 1610 and 1630 cm$^{-1}$ and medium carbonyl bands at 1680 and 1690 cm$^{-1}$. The infrared spectrum was consistent with the amic acid structure.

The xylene filtrate was stripped to dryness and the residue weighed 1.0 gram. The infrared spectrum of the residue had a strong carbonyl band at 1720 cm$^{-1}$ and a weak carbonyl band at 1780 cm$^{-1}$. These bands are consistent with the imide structure and indicate some of the amic acid cyclized to N-(2,2,6,6-tetramethyl-4-piperidinyl)-1,4,5,6,7,7-hexachloro-5-norbornene-2,3-dicarboximide.

A sample of the xylene insoluble product was heated in a Perkin-Elmer DSC under nitrogen to 250° C. A comparison of FTIR scans of the material before and after heating to 250° C. indicated the carbonyl peaks at 1680 and 1690 cm$^{-1}$ had disappeared, the carbonyl peaks at 1610 and 1630 cm$^{-1}$ became very weak upon heating and a very strong imide peak formed at 1720 cm$^1$, indicating the xylene insoluble amic acid had been converted to N-(2,2,6,6-tetramethyl-4-piperidinyl)-1,4,5,6,7,7-hexachloro-5-norbornene-2,3-dicarboximide.

EXAMPLE VII

Reaction of Tetrachlorophthalic Anhydride with Beta-[2,2,6,6-tetramethyl-4-piperidinylamino]propionic Acid Hydrazide (A) In Tetrahydrofuran at 35° C.:

Into a 125 ml Erlenmeyer flask, 2.86 grams (0.01 mole) tetrachlorophthalic anhydride and 50 ml of tetrahydrofuran were added. The mixture was warmed to 35° C. and stirred with a magnetic stirring bar until the anhydride dissolved. To the stirred solution, 2.42 grams (0.01 mole) beta-(2,2,6,6-tetramethyl-4-piperidinylamino)propionic acid hydrazide were added slowly over a few minutes. A white precipitate quickly formed. The slurry was stirred an additional 1-2 hours at 25°-35° C. and filtered. The filter cake weighed 5.2 grams after drying overnight on a watch glass. An infrared scan of the product (nujol mull) contained a strong carbonyl band at 1625 cm$^{-1}$. The infrared spectrum was consistent with the amic acid structure, indicating the product was beta-(2,2,6,6-tetramethyl-4-piperidinylamino)-N-[(2-carboxy-3,4,5,6-tetrachloro)-benzoylamino]propionamide. The product had a melting point of 162°-164° C.

(B) In Refluxing Xylene:

Into a 250 ml 3-neck round bottom flask, 6.3 grams (0.022 mole) tetrachlorophthalic anhydride, 6.1 grams (0.025 mole) beta-[2,2,6,6-tetramethyl-4-piperidinylamino]propionic acid hydrazide and 130 ml xylene were added. The flask was equipped with a magnetic stirrer, thermometer and Dean Stark trap containing a reflux condenser. The reaction mixture was heated in an oil bath to reflux and azeotroped for 2 hours at approximately 140° C. The reaction mixture was cooled and the insoluble components were filtered off. The filter cake was slurried in hexane, refiltered and the filter cake was air dried. The product was a brownish-red powder weighing 3.7 grams. The infrared spectrum of the product had a strong broad carbonyl band at 1635 cm$^{-1}$ and was similar to that of the product obtained in Example VIIA. The infrared spectrum was consistent with the amic acid structure indicating the xylene insoluble product was predominantly beta-(2,2,6,6-tetramethyl-4-piperidinylamino)-N-[(2-carboxy-3,4,5,6-tetrachloro)benzoylamino]propionamide.

The xylene filtrate was stripped to dryness on a rotary evaporator under reduced pressure. The yellow powder weighed 8.2 grams and had melting point of 183°-186° C. The infrared spectrum of the material had strong carbonyl bands at 1745 and 1720 cm$^{-1}$ and was consistent with the tetrachlorophthalimide structure, indicating the xylene soluble product was predominantly beta-(2,2,6,6-tetramethyl-4-piperidinylamino)-N-(tetrachlorophthalimido)propionamide.

(C) Conversion of the Amic Acid of Example VIIA to the Imide of Example VIIB:

A sample of the amic acid prepared in Example VIIA was heated in the DSC as in Example ID. The DSC scan indicated a reaction began occurring around 146° C. and the reaction peaked at 187° C. A comparison of FTIR scans of the material before and after heating to 190° C. showed that most of the broad strong carbonyl band at 1625 cm$^{-1}$ had converted into two strong sharp bands at 1745 and 1720 cm$^{-1}$. The FTIR scan of the heated sample was consistent with the imide structure and the xylene soluble product prepared in Example VIIB.

EXAMPLE VIII

Reaction of Tetrabromophthalic Anhydride with Beta-[2,2,6,6-tetramethyl-4-piperidinylamino]propionic Acid Hydrazide (A) In Tetrahydrofuran at 35° C.:

The reaction was carried out in the same manner as in Example VIIA except 4.64 grams (0.01 mole) tetrabromophthalic anhydride was used instead of the tetrachlorophthalic anhydride. The filter cake weighed 6.2 grams after drying overnight on a watch glass. An infrared scan of the product (nujol mull) contained a strong broad carbonyl band at 1620 cm$^{-1}$. The infrared spectrum was consistent with the amic acid structure, indicating the product was predominantly beta-(2,2,6,6-tetramethyl-4-piperidinylamino)-N-[(2-carboxy-3,4,5,6-tetrabromo)benzoylamino]propionamide. The product melted at 165°-267° C.

(B) In Refluxing Xylene:

The reaction was carried out in the same manner as in Example VIIB except 9.1 grams (0.022 mole) of tetrabromophthalic anhydride was used instead of the tetrachlorophthalic anhydride. The reaction mixture was cooled and the xylene insoluble components were filtered off, rinsed with hexane and air dried. The insoluble components weighed 6.4 grams. The infrared spectrum (nujol mull) of the insoluble components had a broad carbonyl peak at 1640 cm$^{-1}$ and was similar to the infrared scan of the product obtained in Example VIIA, indicating the insoluble components were predominantly the amic acid.

The xylene filtrate was stripped to dryness on a rotating evaporator under reduced pressure. The residue was a yellow powder weighing 8.2 grams and had a melting point of 215°–218° C. The infrared spectrum of the xylene soluble product had strong carbonyl bands at 1745 and 1710 cm$^{-1}$ and weaker bands at 1770 and 1650 cm$^{-1}$. The strong carbonyl peak at 1715 cm$^{-1}$ was consistent with the tetrabromophthalimide structure, indicating the xylene soluble product was predominantly beta-(2,2,6,6-tetramethyl-4-piperidinylamino)-N-(tetrabromophthalimido)propionamide.

(C) Conversion of the Amic Acid of Example VIIIA to the Imide of Example VIIIB:

A sample of the amic acid prepared in Example VIIIA was heated in the DSC as in Example ID. The DSC scan indicated that a reaction began occurring around 145° C. and the reaction peaked at 180° C. A comparison of FTIR scans of the material before and after heating to 186° C. showed that most of the strong carbonyl band at 1620 cm$^{-1}$ had converted into strong sharp bands at 1745 and 1710 cm$^{-1}$. The FTIR scan of the heated sample was consistent with the imide structure and the xylene soluble product produced in Example VIIIB.

EXAMPLE IX

Reaction of Chlorendic Anhydride with Beta-(2,2,6,6-tetramethyl-4-piperidiylamino)propionic Acid Hydrazide Into a 125 ml Erlenmeyer flask, 3.70 grams (0.01 mole) chlorendic anhydride and 50 ml of tetrahydrofuran were added. The mixture was warmed to 35° C. and stirred with a magnetic stirring bar until the anhydride completely dissolved. 2.42 grams (0.01 mole) beta-(2,2,6,6-tetramethyl-4-piperidinylamino)propionic acid hydrazide were stirred into the solution. The hydrazide dissolved in the solution and no precipitation occurred. The solution was allowed to stand overnight but still no precipitation had occurred. An infrared scan was run on the solution, which indicated that the anhydride had completely reacted.

The tetrahydrofuran was stripped off on a rotary evaporator under reduced pressure. The off-white residue was scraped out of the flask and pulverized. The product weighed 7.1 grams and melted at 138°–140° C. An infrared spectrum of the product (nujol mull) contained a strong carbonyl band at 1630 cm$^{-1}$ and a weaker band at 1605 cm$^{-1}$. The infrared spectrum was consistent with the amic acid structure, indicating the product was predominantly beta-(2,2,6,6-tetramethyl-4-piperidinylamino)-N-[(3-carboxy-1,4,5,6,7,7-hexachloro-5-norbornene)-2-carbonylamino]propionamide.

A sample of the amic acid was heated on the DSC as in Example ID. The DSC scan indicated a reaction began occurring around 120° C. and the reaction peaked at 145° C. A comparison of FTIR scans of the material before and after heating to 151° C. showed that most of the strong carbonyl bands at 1630 and 1605 cm$^{-1}$ had converted into strong sharp bands at 1745 and 1705 cm$^{-1}$. The FTIR scan of the heated sample was consistent with the imide structure, indicating most of the amic acid had cyclized to the imide.

EXAMPLE X

Reaction of Tetrabromophthalic Anhydride with N-(1-acetyl-2,2,6,6-tetramethyl-4-piperidinyl)-N'-aminooxamide Into a 250 ml 3-neck round bottom flask 14.0 g (0.03 mole) of tetrabromophthalic anhydride and 130 ml of xylene were added. The flask was equipped with a magnetic stirrer, thermometer and Dean Stark trap containing a reflux condenser. The mixture was warmed to 70° C. to dissolve the anhydride and then 8.55 g (0.03 mole) of N-(1-acetyl-2,2,6,6-tetramethyl-4-piperidinyl)-N'-aminooxamide were added over about 5 minutes. The reaction mixture was heated to reflux and azeotroped for 1.5 hours. The reaction mixture was cooled to 70° C. and the solids were filtered off. The filter cake was slurried in hexane, refiltered and air dried overnight. The resultant tan powder weighed 5.1 g and had a melting point of 254°–256° C. The infrared spectrum (nujol mull) of the filter cake had a strong carbonyl band at 1745 cm$^{-1}$. It also had a strong carbonyl band at 1655 cm$^{-1}$ with a weak shoulder at 1620 cm$^{-1}$.

The light yellow xylene filtrate was stripped to dryness on a rotary evaporator under reduced pressure. The residue was scraped out of the flask, pulverized by mortar and pestle, slurried in hexane, filtered and air dried. The light yellow powder weighed 17.0 g. The infrared scan (nujol mull) of the yellow powder had a strong carbonyl band at 1745 cm$^{-1}$, a strong carbonyl band at 1665 cm$^{-1}$ and a moderate band at 1610 cm$^{-1}$. The infrared scans indicated that both products were predominantly in the imide form with some uncyclized amic acid present.

EXAMPLE XI

Reaction of Tetrachlorophthalic Anhydride with N-(1-acetyl-2,2,6,6-tetramethyl-4-piperidinyl)-N'-aminooxamide This reaction was carried out in the same manner as Example X except 8.57 g (0.03 mole) of tetrachlorophthalic anhydride were substituted for the tetrabromophthalic anhydride. The reaction was azeotroped 1.5 hours, cooled to 70° C. and filtered to remove a small amount of brownish-red solids, which were discarded. The filtrate was cooled to room temperature and the solids that formed were filtered off, slurried in hexane, refiltered and air dried. The product (first sample) was a light tan powder that weighed 13.2 g.

The xylene filtrate was stripped to dryness, slurried in 30 ml xylene and filtered. The filter cake was reslurried in hexane, refiltered and air dried. This product (second sample) weighed 2.7 g.

The infrared spectra (nujol mull) of both samples were essentially the same. They contained a strong carbonyl band at 1740 cm$^{-1}$, a moderately strong doublet at 1690 and 1660 cm$^{-1}$ and a moderate band at 1610 cm$^{-1}$.

The infrared scans indicated that both products were predominantly N-(1-acetyl-2,2,6,6-tetramethyl-4-piperidinyl)-N'-(3,4,5,6tetrachlorophthalimido)oxamide.

EXAMPLE XII

Preparation of N-(1-acetyl-2,2,6,6-tetramethyl-4-piperidinyl)tetrabromophthalimide Into a 500 ml 3-neck flask, 28.0 grams (0.06 mole) tetrabromophthalic anhydride and 150 ml of acetic acid were added. The flask was equipped with a magnetic stirrer, thermometer, reflux condenser and dropping funnel containing 10.0 grams (0.06 mole) 4-amino-2,2,6,6-tetramethylpiperidine. The 4-amino-2,2,6,6-tetramethylpiperidine was added dropwise to the stirring slurry of tetrabromophthalic anhydride. After the addition of the amine was complete, the reaction mixture was cooled to 15° C., whereupon the mixture solidified. The gelatinous material was scraped out of the flask and filtered. The filter cake was slurried in 400 ml hexane and refiltered. The filter cake was spread out on a watch glass and air dried for 2 days. The dry product weighed 36.1 grams. The product partially melted at 265° C. and then resolidified and did not melt below 290° C. An infrared scan (nujol mull) of the material had a weak carbonyl band at 1705 cm$^{-1}$ and a strong carbonyl doublet at 1660–1675 cm$^{-1}$ and a sharp medium intensity band at 1620 cm$^{-1}$. The infrared scan was consistent with the structure of the acetic acid salt of N-(2,2,6,6-tetramethyl-4-piperidinyl)tetrabromophthalamic acid.

35.9 grams (0.052 mole) of the amic acid salt prepared above, 4.5 grams (0.055 mole) sodium acetate and 250 ml of acetic anhydride were added into a 500 ml 3-neck flask. The flask was equipped with a thermometer, magnetic stirrer and reflux condenser. The mixture was heated in an oil bath and refluxed for 2 hours. The reaction was cooled to room temperature and the insolubles were filtered off. The filtrate was transferred to a 500 ml round bottom flask and the excess acetic anhydride was stripped off on a rotary evaporator under reduced pressure. The residue was dissolved in 300 ml methylene chloride. The methylene chloride solution was carefully washed with a saturated sodium bicarbonate solution to remove any residual acetic acid or acetic anhydride. The methylene chloride solution was dried over anhydrous sodium sulfate, filtered and the methylene chloride was stripped off. The residue was slurried in 300 ml of methanol and filtered. The filter cake was reslurried in another 300 ml of methanol heated to reflux and then filtered while hot. The filter cake was air dried overnight and weighed 21.0 grams. The product had a melting range of 236 -243° C. An infrared scan (nujol mull) of the product contained strong carbonyl bands at 1700 cm$^{-1}$ and 1615 cm$^{-1}$. The IR scan was consistent with the imide structure.

EXAMPLE XIII

Preparation of N-(1-acetyl-2,2,6,6-tetramethyl-4-piperidinyl)-tetrachlorophthalimide The acetic acid salt of N-(2,2,6,6-tetramethyl-4-piperidinyl)tetrachlorophthalamic acid was prepared by refluxing 7.8 grams (0.05 mole) of 4-amino-2,2,6,6-tetramethylpiperidine, 14.3 grams (0.05 mole) of tetrachlorophthalic anhydride in 100 ml of acetic anhydride for 4 hours. The acetic anhydride was stripped off on a rotary evaporator under reduced pressure. The light yellow residue was slurried in 300 ml hexane and filtered. The filter cake was reslurried in fresh hexane and refiltered. The filter cake was air dried for 3 days on a watch glass. The dried product weighed 26.5 grams.

Into a 250 ml 3-neck flask, 11.0 grams (0.022 mole) of the amic acid salt prepared above, 1.8 grams (0.022 mole) of sodium acetate and 100 ml of acetic anhydride were added. The flask was equipped with a magnetic stirrer, thermometer and reflux condenser. The reaction was stirred and heated to 120° C. in an oil bath to dissolve all the solids. The reaction was stirred an additional 15 minutes at 120° C. and then allowed to cool back to room temperature over 45 minutes. The white solids that came out of solution were filtered off, washed twice with hexane and air dried. The dry product weighed 5.4 grams. An infrared scan (nujol mull) of the product contained strong carbonyl bands at 1710 cm$^{-1}$ and 1595 cm$^{-1}$.

EXAMPLE XIV

Extrusion of Polypropylene with Flame Retardant Hindered Amine Light Stabilizers Dry blends (Runs A through F) of Himont's Profax 6501 polypropylene, the flame retardant hindered amine light stabilizers from Examples X, XI and XII and a small amount of a hindered phenol antioxidant (Irganox 1076) were prepared in a polyethylene container (see Table I for blend compositions of Runs A through F). The blends were shaken well to ensure a good dispersion of the additives in the polypropylene. The blends were then extruded on a Brabender Prep Center Extruder Model No. 1340 having a 1.25 inch screw diameter with a length to diameter ratio of 25:1. The extruder was operated at a screw speed of 20 RPM and all the heating zones were controlled at 220° C. The first 100 grams of extrudate were used to purge the extruder and were discarded. The remaining extrudate was air-cooled and pelletized.

The pelletized extrudate was let down with more polypropylene (2 parts polypropylene to 1 part masterbatch—see Table I) and enough Irganox 1076 to provide a 0.25% concentration in Runs A through C. The blends were shaken well and reextruded at 220° C. and a screw speed of 30 RPM. The extrudates were cooled and pelletized. The concentration of the 2,2,6,6-tetramethylpiperidinyl group was approximately 0.3%.

In Run D, the original extrudate was prepared containing a 0.3% concentration of the 2,2,6,6-tetramethylpiperidinyl group and 0.25% Irganox 1076 so it was not let down any further.

Control samples (Runs E and F) of polypropylene without any light stabilizers were also extruded. One control (Run F) did not contain any additives and the other (Run E) contained Irganox 1076 at the 0.25% level.

The extrudates were injection molded in a Newbury 25 ton injection molding machine at 400° F. into 7⅜"×¾"×⅛" tensile bars.

TABLE I

| | | 1ST EXTRUSION | | | 2ND EXTRUSION | | |
|---|---|---|---|---|---|---|---|
| RUN | EXAMPLE # | FLAME RETARDANT HALS Ex # | POLY-PROPYLENE | IRGANOX 1076 | 1ST EXTRUDATE | ADDITIONAL POLYPROPYLENE | ADDITIONAL IRGANOX 1076 |
| | | grams | grams | grams | grams | grams | grams |
| A | XIV | X | 14.0 | 285 | 0.8 | 150 | 300 | 1.1 |
| B | XV | XI | 10.6 | 285 | 0.8 | 150 | 300 | 1.1 |
| C | XVI | XII | 11.3 | 260 | 0.7 | 150 | 300 | 1.1 |
| D | XVII | XII | 5.5 | 390 | 1.0 | — | — | — |
| E | Control 1 | — | — | 1000 | 2.5 | | | |
| F | CONTROL 2 | — | — | 1000 | — | | | |

EXAMPLE XV

Evaluation of the Flame Retardant Hindered Amine Light stabilizers in the Stabilization of Polypropylene The tensile bars from Example XIV were placed in a QUV Accelerated Weathering Tester (Q Panel Company) for various exposure times. The QUV operated with an 8 hour light cycle (UV-B) at 60° C. and a 4 hour condensation cycle at 50° C. Samples were placed in the QUV and withdrawn at approximately the same time of day during the condensation cycle. The tensile bars were pulled on an Instron and the percent elongation was determined. If a tensile bar snapped immediately under load without undergoing any elongation, that was considered a brittle break. The tensile bars from Runs A-D all survived more than 20 days in the QUV without undergoing a brittle break in the Instron. Control 1 (Run E) containing only Irganox 1076 did not survive 7 days while Control 2 (Run F), which did not contain any additives, did not survive 5 days. The tensile bars from Runs A, B and D still retained approximately 15% of their original elongation after 20 days QUV exposure while the tensile bar from Run C retained only about 5% of its original elongation.

The present invention may be embodied in other specific forms without departing from the spirit or essential attributes thereof and, accordingly, reference should be made to the appended claims, rather than the specification as indicating the scope of the invention.

We claim:

1. A flame retardant light stabilizer comprising a hindered amine light stabilizer having Formula I:

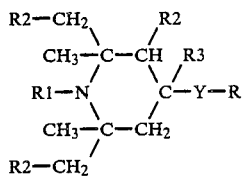

wherein

R is a halogen-substituted flame retardent radical of Formula II, III, IV or V:

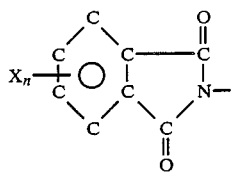

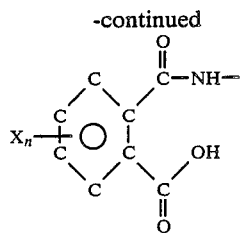

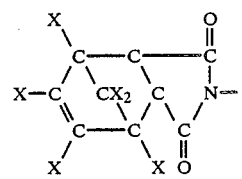

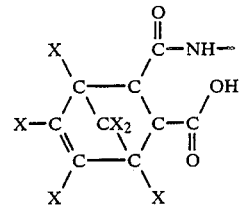

X is chlorine or bromine or a combination thereof;

n is an integer from 1 to 4;

R1 is hydrogen, an alkyl radical of 1 to 20 carbons, an alkenyl radical of 3 to 6 carbons, an aralkyl radical of 7 to 12 carbons, an aliphatic acyl radical of 1 to 10 carbons, an aromatic acyl radical of 7 to 13 carbons, an alkoxy carbonyl radical of 2 to 9 carbons, an aryloxy carbonyl radical of 7 to 13 carbons, a hydroxyalkyl radical of 1 to 5 carbons or an epoxyalkyl radical of 3 to 6 carbons;

R2 is hydrogen or an alkyl radical of 1 to 4 carbons;

R3 is hydrogen, hydroxyl or an alkoxy radical of 1 to 4 carbons;

when R3 is hydrogen, Y is a direct bond, or a divalent radical —Z—R4—C(O)—N(R5)—, —Z—C(O)—N(R5)—, —Z—C(O)—R6—C(O)—N(R5)—, —R4—C(O)—N(R5)— or —C(O)—N(R5)—, where Z is —O—, —N(R7)— or —N(R7)—R8—N(R7)—;

when R3 is hydroxyl or an alkoxy radical, Y is a divalent radical —R4—C(O)—N(R5)— or —C(O)—N(R5)—;

R4 is an alkylene diradical of 1 to 4 carbons;

R5 is hydrogen, a primary alkyl radical of 1 to 8 carbons, a secondary alkyl radical of 3 to 8 carbons, an aralkyl radical of 7 to 12 carbons or a cycloalkyl radical of 5 to 12 carbons;

R6 is a direct bond, a substituted or unsubstituted alkylene diradical of 1 to 14 carbons, a substituted or unsubstituted oxydialkylene diradical of 4 to 20 carbons, a substituted or unsubstituted thiodialkylene diradical of 4 to 10 carbons, a substituted or unsubstituted alkenylene diradical of 2 to 10 carbons, or a substituted or unsubstituted o-, m- or p-phenylene diradical, the R6 substituents comprising a lower alkyl radical of 1 to 4 carbons, a lower alkoxy radical of 1 to 4 carbons, hydroxy, bromine, chlorine a mercapto radical or a lower alkylmercapto radical of 1 to 4 carbons;

R7 is hydrogen, an alkyl radical of 1 to 10 carbons, an aryl radical of 6 to 12 carbons, an aralkyl radical of 7 to 12 carbons or a cycloalkyl radical of 5 to 12 carbons; and R8 is an alkylene diradical of 2 to 12 carbons.

2. A polymer composition comprising a flammable thermoplastic resin which is subject to photooxidative degradiation and a light stabilizer flame retardant according to claim 1, the light stabilizing flame retardant being present in an amount effective to stabilize the polymer composition from the effects of photooxidation and effective to decrease the flammability of the polymer composition.

3. The polymer composition according to claim 2, wherein the thermoplastic resin is polystyrene, polyolefin, nylon, polycarbonate, poly(phenylene oxide), polyester, polyacrylate or polyamide.

4. The polymer composition according to claim 2, wherein the light stabilizing flame retardant is present in an amount of about 0.5% to about 5.0% by weight relative to the polymer composition.

5. The light stabilizing flame retardant according to claim 1, wherein R is 2-carboxytetrabromobenzoylamino, 2-carboxytetrachlorobenzoylamino, 1,4,5,6,7,7-hexachloro-5-norborene-3-carboxy-2-carbonylamino, tetrabromophthalimido, tetrachlorophthalimido or 1,4,5,6,7,7-hexachloro-5-norbornene-2,3-dicarboximido; R1 is hydrogen, methyl, acetyl, benzoyl, 2-hydroxyethyl, phenoxycarbonyl or benzyl; R2 is hydrogen or methyl; R3 is hydrogen; Y is a direct bond, a diradical —Z—R4—C(O)—N—(R5)— or —Z—C(O)—R6—C(O)—N(R5)—; Z is —N(R7)—, R4 is —(CH2)$_b$—, R5 and R7 are hydrogen, R6 is a direct bond or —(CH2)$_b$—; and b is 1 or 2.

6. The light stabilizing flame retardant according to claim 1, wherein R is tetrabromophthalimido; R1 is hydrogen; Y is a direct bond, a diradical —Z—R4—C(=O)—N(R5)— or —Z—C(=O)—R6—C(=O)—N(R5)—; Z is —N(R7)—; R2, R3, R5 and R7 are hydrogen; R4 is —(CH2)$_b$—; R6 is a direct bond; and b is 1 or 2.

7. The light stabilizing flame retardant according to claim 1, further comprising the acid addition salt of the light stabilizer having a Formula VI:

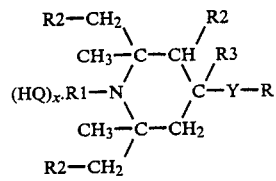

VI wherein
Q is R9—C(=O)—O$^-$;
R9 is an alkyl radical of 1 to 4 carbons;

and x is 0 or 1, with the proviso that x is 0 when R1 is an acyl radical, an alkoxycarbonyl radical or an aryloxycarbonyl radical.

8. The light stabilizing flame retardant according to claim 7, wherein R is 2carboxytetrabromobenzoylamino, 2-carboxytetrachlorobenzoylamino, 1,4,5,6,7,7-hexachloro-5-norbornene-3-carboxy-2-carbonylamino, tetrabromophthalimido, tetrachlorophthalimido or 1,4,5,6,7,7-hexachloro-5-norbornene-2,3-dicarboximido; R1 is hydrogen, methyl, acetyl, benzoyl, 2-hydroxyethyl, phenoxycarbonyl or benzyl; R2 is hydrogen or methyl; R3 is hydrogen; Y is a direct bond, a diradical —Z—R4—C(=O)—N—(R5)— or —Z—C(=O)—R6—C(=O)—N(R5)—; Z is —N(R7)—, R4 is —(CH2)$_b$—, R5 and R7 are hydrogen, R6 is a direct bond or —(CH2)$_b$—; and b is 1 or 2; HQ is acetic acid; and x is 0 or 1 when R1 is hydrogen, a methyl radical, a 2-hydroxyethyl radical or a benzyl radical.

9. The light stabilizing flame retardant according to claim 8, wherein R is tetrabromophthalimido, R1 is hydrogen or methyl; Y is a direct bond, a diradical —Z—R4—C(=O)—N(R5)— or —Z—C(=O)—R6—C(=O)—N(R5)—; Z is —N(R7)—; R2, R3, R5 and R7 are hydrogen; R4 is —(CH2)$_b$—; R6 is a direct bond; and b is 1 or 2; HQ is acetic acid and X is 0 or 1.

10. The light stabilizing flame retardant compound according to claim 1, wherein the light stabilizing flame retardant is N-(2,2,6,6-tetramethyl-4-piperidinyl)-N'-(3,4,5,6-tetrabromophthalimido)oxamide, N-(2,2,6,6-tetramethyl-4-piperidinyl)-N'-(3,4,5,6-tetrachlorophthalimido)oxamide, N-(2,2,6,6-tetramethyl-4-piperidinyl)tetrabromophthalimide, N-(2,2,6,6-tetramethyl-4-piperidinyl)tetrachlorophthalimide, N-(1-acetyl-2,2,6,6-tetramethyl-4-piperidinyl)-N'-(tetrabromophthalimido)oxamide, N-(1-acetyl-2,2,6,6-tetramethyl-4-piperidinyl)-N'-(3,4,5,6-tetrachlorophthalimido) oxamide, N-(1-acetyl-2,2,6,6-tetramehtyl-4-piperidinyl)-N'-(3,4,5,6-tetrachlorophthalimido)oxamide, or N-(1-acetyl-2,2,6,6-tetramethyl-4-piperidinyl)-N'-(3,4,5,6-tetrachlorophthalimido)oxamide.

11. The acetic acid addition salt of the light stabilizing flame retardant according to claim 10.

12. A method for preparing the light stabilizing flame retardant according to claim 1, comprising reacting a halogen-substituted flame retardant of Formula VII or VIII:

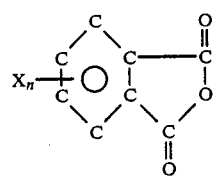

VII

-continued

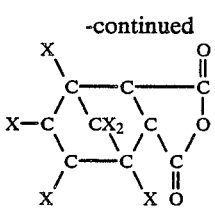
VIII wherein X is chlorine or bromine or combinations thereof and n is an integer from 1 to 4, with a light stabilizer of Formula IX having a hindered amine light stabilizing group, a primary amino group or a reactive hydrazido group:

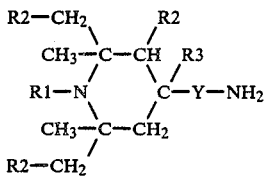
IX at about room temperature to about 175° C. for about 30 seconds to about 48 hours to form an (acylamino)amic acid.

13. The method according to claim 12, further comprising heating the (acylamino)amic acid to about 100° C. to about 300° C. for about 30 seconds to about 48 hours to form an (acylamino)imide.

14. The method according to claim 13, wherein the amic acid is heated to about 125° C. to about 225° C. to form the (acylamino)imide.

15. The method according to claim 12, wherein the molar ratio of flame retardant to light stabilizer is about 0.9:1 to about 1:0.9.

16. The method according to claim 17, wherein the reaction occurs in the presence of an inert solvent selected from the group consisting of toluene, xylene, chlorobenzene, mesitylene, dimethylformamide, tetrahydrofuran, N-methyl-2-pyrrolidone, dimethylacetamide and acetic acid.

17. The method according to claim 12, wherein the reaction occurs in the presence of an inert molten polymer selected from the group consisting of polystyrene, rubber-modified polystyrene, halogenated polystyrene, polyethylene, polypropylene, graft copolymer of styreneacrylonitrile on butadiene rubber, styreneacrylonitrile copolymer, graft copolymer of styrene-methyl methacrylate on polybutadiene rubber, styrene-acrylonitrile copolymer modified with acrylic ester polymer, poly(phenylene oxide) and poly(phenylene ether).

18. The method according to claim 13, wherein the reaction occurs in a polymer extruder.

* * * * *